United States Patent [19]

Carlock

[11] 4,173,575

[45] Nov. 6, 1979

[54] POLYMER BOUND (PENTAHAPTOCYCLOPENTADIENYL) BIS CARBONYL RHODIUM HYDROFORMYLATION CATALYST

[75] Inventor: John T. Carlock, Ponca City, Okla.

[73] Assignee: Continental Oil Company, Ponca City, Okla.

[21] Appl. No.: 877,440

[22] Filed: Feb. 13, 1978

[51] Int. Cl.² ............................................. C07F 15/00
[52] U.S. Cl. ......................... 260/429 R; 260/604 HF; 252/431 C; 252/431 P
[58] Field of Search ................... 260/429 R, 429 CY; 252/431 R

[56] References Cited

U.S. PATENT DOCUMENTS

| | | | |
|---|---|---|---|
| 3,636,122 | 1/1972 | Cramer et al. | 260/429 R |
| 3,644,446 | 2/1972 | Booth et al. | 260/429 R |
| 3,859,359 | 1/1975 | Keblys | 260/429 R X |
| 3,965,192 | 6/1975 | Booth | 260/429 R X |
| 3,998,864 | 12/1976 | Trevillyan | 260/429 R X |
| 4,062,883 | 12/1977 | Hawthorne et al. | 260/429 R |

*Primary Examiner*—Helen M. S. Sneed

*Attorney, Agent, or Firm*—Cortlan R. Schupbach, Jr.

[57] ABSTRACT

A catalyst having the structural formula

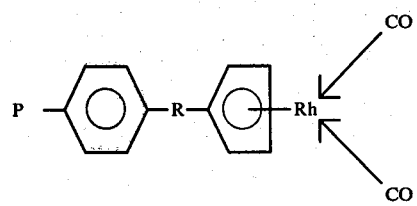

wherein R is 0 or an alkyl having from 1 to 10 carbon atoms and wherein Ⓟ is a polystyrene polymer backbone, where the 6-member ring is part of the polymer. The catalyst is useful for converting olefins to aldehydes in high yield under reaction temperatures of from about 90° to 140° C. and pressures of about 300 to about 5000 psig in the presence of hydrogen and carbon monoxide yielding gases, and preferably polymer swelling solvents such as benzene, THF and toluene. The catalyst is also useful in hydrogenation reactions.

9 Claims, No Drawings

POLYMER BOUND (PENTAHAPTOCYCLOPENTADIENYL) BIS CARBONYL RHODIUM HYDROFORMYLATION CATALYST

This invention relates to the synthesis of a novel polymer bound rhodium-containing catalyst. More particularly, this invention relates to the synthesis and catalytic activity of a novel polymer bound rhodium-containing hydroformylation catalyst containing the active rhodium as a (pentahaptocyclopentadienyl)biscarbonyl complex bound to the polymer.

Hydroformylation of terminal olefins by homogeneous rhodium catalysts is well-known in the art. Representative examples of references describing the types of rhodium catalysts used in hydroformylation reaction and reaction conditions are U.S. Pat. Nos. 3,917,661; 3,907,847; 3,821,311; 3,499,932; 3,527,809; 3,825,601; 3,948,999; and 3,984,478. Literature references include Tetrahedron Letters, 1971 (50) 4787–90; Grubbs et al. J. Macromol. Sci., Chem, 1973, 7 (5) 1047–63; Inorg. Chem. Acta, 1975, 12 (1), 15–21, Grubbs et al. Polym. Prepr. ACS Div. Polymer Chem., 1972, 13 (12), 828–32, and Japan Kokai 76 06,890. While these references are not exhaustive of the art, they appear to be representative of hydroformylation in the current state of this art. However, these catalysts and reactions are generally poor when used with internal olefins. In addition, the catalysts disclosed in the referenced patents are extremely difficult to recover from the reaction. This recovery is important since rhodium is an extremely expensive metal and the product cost rises sharply with each percentage drop in rhodium recovery from a previous reaction. Additionally, these catalysts usually employ very toxic ligands such as Group V materials, phosphines, phosphites, arsines, arsinites and organoantimony compounds.

Hydroformylation is a reaction which converts olefins to aldehydes such as shown in the formula below.

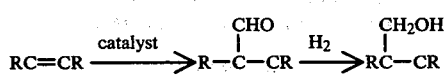

wherein R is hydrogen or an alkyl.

Usually the hydroformylation procedure is followed by the hydrogenation of aldehydes to produce alcohols. This procedure is relatively simple and can be carried out by any one of several well-known means. The most difficult and least efficient step is the initial hydroformylation conversion of olefins to aldehydes. In the art cited above, such conversions have been accomplished, but only using catalysts which are difficult to recover, and in some cases are extremely toxic.

It would therefore be of great benefit to provide a catalyst which has high levels of activity for the conversion of olefins to aldehyde, employs non-toxic materials, and is readily recovered.

It is therefore an object of the present invention to provide a synthesis and catalyst for hydroformylation reactions which is recoverable and reuseable. Other objects will become apparent to those skilled in this art as the description proceeds.

It has now been discovered according to the present invention that a catalyst having the general structure

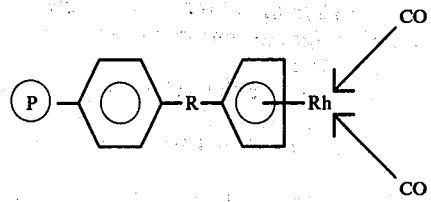

wherein R is O or an alkyl group containing from 1 to 10 carbon atoms, and where ⓟ represents a polystyrene polymer backbone, the 6-member ring being part of the polymer, is an effective catalyst for the hydroformylation conversion of olefins to aldehydes. The catalyst is effective under conversion conditions wherein the temperature ranges from about 90° C. to about 140° C. and pressures of from about 300 to about 5,000 pounds per square inch gauge (psig). Higher temperatures are possible as the pressure exceeds 2,500 psig. High temperatures without sufficient pressure will generally deactivate the catalyst. The reaction is carried out in the presence of mixtures of hydrogen and carbon monoxide. Normally the ratio of hydrogen to carbon monoxide will range from about 80/20 to about 20/80 although from about 60/40 to about 50/50, respectively, is preferred.

The catalyst of the instant invention is an unique polymer bound (pentahaptocyclopentadienyl) biscarbonylrhodium compound useful in hydroformylation reactions. The material is effective for both internal and primary olefins and does not employ a potentially toxic group V ligand. The catalyst is also effective for the hydrogenation of the aldehyde produced by hydroformylation to form alcohols.

The polystyrene polymer to which the active rhodium catalyst complex is bonded can be any polymer of sufficient molecular weight to contain the levels of rhodium desired in the reaction being carried out. Normally, however, the polymer will have a molecular weight of at least 4,000. Generally polymers having a molecular weight of 4,000 to 100,000 are most preferred. Representative examples of acceptable polystyrene polymers are Biorad SX-1 and SX-2 (trademark of and sold by Biorad laboratories, Richmond, California), XAD-2, XAD-4 (trademark of and sold by Rhom and Haas Co), and Dow Chemical Companies styrene macroreticular copolymer (20% divinylbenzene). In general, the backbone can comprise any crosslinked or macroreticular polymer having available phenyl rings. Polystyrene containing polymers are preferred.

The catalyst of the instant invention can be prepared, when R is an alkyl group containing from 1 to 10 carbon atoms, as follows (a) a halo-methylated polystyrene is added to Group I metal M-cyclopentadiene wherein M is selected from the group consisting of sodium, potassium or lithium, in a suitable solvent to form a mixture;

(b) stirring the mixture of (a) for a period of time sufficient to effect reaction, then filtering the reaction solution and extracting the retained polymer on the filter with a suitable solvent, and drying the polymer;

(c) stirring the recovered polymer into a suitable solvent and adding an alkyl or aryl organolithium material containing from 1 to 10 carbon atoms and containing agitation for a period of time sufficient to effect reaction;

(d) filtering the polymer from solution, readding to a suitable solvent, and adding [Rh(CO)₂X]₂ wherein X is selected from the group consisting of chlorine, bromine and iodine, and (e) stirring the material for sufficient time to effect reaction and removing the catalyst from solution by extracting with a suitable solvent, and drying prior to use.

The entire synthesis of the catalyst must be carried out under a dry inert atmosphere usually consisting of nitrogen, argon, helium, xenon and neon, and the like. Any recovery and handling is also carried out in an oxygen and water-free environment to prevent catalyst inactivity. Representative examples of suitable solvents in the instant invention are benzene, tetrahydrofuran (THF), acetophenone, dimethylformamide (DMF) and ethanol/benzene mixtures. All solvents used must be dry and oxygen-free.

Representative examples of the alkyl or aryl organo lithium material are n-butyl lithium, methyl lithium, s-butyl lithium, t-butyl lithium, ethyl lithium, propyl lithium, and phenyl lithium.

When the general structural formula of the catalyst has R=O another method of preparation is necessary. Generally the procedure comprises, under a dry, inert atmosphere, swelling a halogenated polystyrene with a suitable solvent, cooling and adding sodium, lithium or potassium cyclopentadieneide together with rapid stirring. The stirred mixture is then allowed to warm to room temperature and stirring is continued for sufficient time for the reaction to take place. The resulting polymer is then removed and washed with a suitable solvent, refiltered and redryed yielding a modified polymer having the following structure

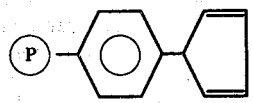

Procedures for obtaining this polymer can be found at: W. D. Bonds, Jr., CH Brubaker, Jr., E. S. Chandrasekran, C. Gibbons, R. H. Grubbs, and L. C. Kroll. "*Polystyrene Attached Titanocene Species Preparation and Reactions*", J. Amer Chem Soc., 97, 2128 (1975); J. M. J. Frechet and M. J. Farrall. "*Functionalization of Crosslinked Polystyrene Resins by Chemical Modification: A Review*" from *Chemistry and Properties of Crosslinked Polymer*, Academic Press (1977) New York, Page 59, and R. H. Grubbs, "*Hybrid-phase Catalysts*", *Chemtech*, 7, 512 (1977).

The recovered polymer is then swollen in a suitable solvent and an alkyl or aryl organo lithium material is added. The mixture is stirred for a sufficient period of time for reaction to occur and is then filtered, washed with a suitable solvent, and refiltered yielding a material having the general structure

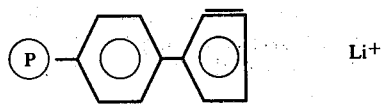

However obtained, the recovered polymer is then added to a suitable solvent, and a weight of [Rh(CO)₂ X]₂ equal to (0.5)(L)(M)(A)(W) is added to the stirring solution, wherein;

L is equal to the moles of C₅H₅ substitution per gram of polymer;

M is equal to the grams of polymer being converted;

A is the percent desired rhodium substitution expressed as a decimal; and

W equals the molecular weight of the [Rh(CO)₂X]₂ compound. The use of this calculation in either catalyst synthesis allows variation of the Rh content of the finished catalyst. X represents a halogen such as chlorine, bromine or iodine. Chlorine is the halogen of choice.

The [Rh(CO)₂X]₂ material is then added to the stirred solution. The stirring is continued for a sufficient period of time to effect reaction and the filtered product is then extracted with a suitable solvent and dried at high vacuum and room temperature yielding a polymeric catalyst having the structure

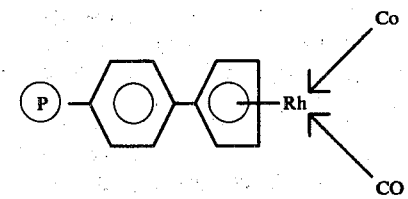

Representative examples of suitable solvents useful for the extraction steps of the catalyst synthesis are xylenes, benzene, toluene, tetrahydrofuran and dimethylformamide. However, any solvent which will effect these functions without destroying the catalyst is, of course, effective.

The invention is more concretely described with reference to the examples below wherein all parts and percentages are by weight unless otherwise specified. The examples are provided to exemplify the instant invention and not to limit it.

Example 1 shows the preparation of the catalyst of the instant invention. Examples 2, 3, 4, and 5 are subsequent conversions of olefins to aldehydes using the catalyst of the instant invention, wherein the catalyst is recovered from one reaction to the next.

EXAMPLE 1

All work was conducted in an argon filled oxygen-free dry box except for the actual hydroformylation, which was carried out under CO/H₂ atmospheres in the autoclave. The solvents employed were of anhydrous grade and were used without further purification. Five grams of 1% cross-linked chloromethylated polystyrene containing 11 percent chloride (Biorad SX-1, trademark of and sold by Biorad Laboratories, Richmond, California) were added to 3.5 grams (0.0486 moles) of lithium cyclopentadienide in 100 milliliters (ml) of tetrahydrofuran (THF). The resulting mixture was stirred for 144 hours and then filtered and extracted with acetone for 18 hours. The polymer was dried at 60° C. at a pressure of 1 torr. Recovery of 5.25 grams of a polymer having the structure

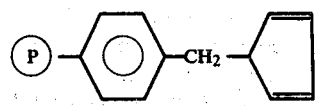

was obtained. Chloride analysis showed the presence of 0.29% chlorine. This substituted polymer was then stirred in 150 ml of THF for one hour at which time 130 ml of 1.6 molar n-butyl lithium was added, and the resulting mixture was stirred in a Schlenk mixing tube (glass-ware designed for air-free handling of sensitive compounds) at 21° C. for 18 hours. The treated polymer was filtered, washed with 500 ml of THF, refiltered, added to 200 ml of THF in a Schlenk mixing tube, and 1.5 grams of [Rh(CO)₂ Cl]₂ (0.0077 mole) was added to the stirring polymer. The resulting mixture was stirred for 72 hours, then filtered and extracted with benzene for 10 hours. The polymer was dried at 25° C. at 0.01 torr for 24 hours yielding 4.5 grams of catalyst having the structure

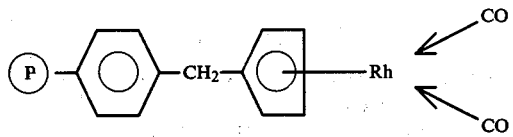

wherein Ⓟ represents the polystyrene polymer backbone. Chemical analysis showed the rhodium treated polymer to have the structure set forth above, with 5.8% rhodium present.

EXAMPLE 2

In an argon filled dry box a stainless steel autoclave was charged with one gram of the polymeric catalyst described in Example 1 (0.56 millimoles rhodium (mMRh) followed by 25 ml of benzene. The catalyst was allowed to swell for 30 minutes. At the end of this time 35 grams (0.17 mole) of 7-tetradecene was added and the reaction pressure was adjusted to 950 pounds per square inch gauge (psig) with a 50/50 mixture of hydrogen and carbon monoxide. The reaction mixture was heated to 120° C. and stirred for 3½ hours. Product analysis using vapor phase chromatography showed 95% conversion to $C_{15}$ aldehydes. Fifteen percent of the aldehyde product was identified as n-pentadecanal. Thus it is shown that the catalyst of the instant invention converts a portion of the internal olefins to primary aldehydes.

EXAMPLE 3

The catalyst was recovered from Example 2 by filtration and rerun identically with Example 2 procedure. After 3½ hours of reaction time analysis showed 96% conversion of the olefins to $C_{15}$ aldehydes. Again, about 15% of the entire product was n-pentadecanal.

EXAMPLE 4

The catalyst was recovered from Example 3 by filtration and rerun identically with Example 2 except that 30 grams of $C_{13},C_{14}$ olefins recovered from the Olex process (Olex is a trademark of Universal Oil Products Company, designating olefins produced from their Molex process, which is also a trademark of Universal Oil Products). After 5 hours of reaction time approximately 30% conversion of olefins to aldehydes was observed. Olefins contained from the Olex process contain aromatic and diene contamination.

EXAMPLE 5

The catalyst was recovered from Example 4 by filtration and rerun identically with Example 2. After four hours of reaction time analysis showed that 96% conversion of olefins to $C_{15}$ aldehydes had occured. Again, about 15% of the entire product was n-pentadecanal.

Example 6 and 7 show the effect of a swelling solvent on the polymeric backbone as relates to the efficiency of the catalysts. In Example 6 a hydroformylation conversion of 7-tetradecene was carried out with unswollen catalyst. Example 7 shows swollen catalyst effect on 1-dodecene hydroformylation.

EXAMPLE 6

An autoclave in an argon filled glove box was charged with 35 grams (0.17 moles) of 7-tetradecene and 1 gram of catalyst. The reactor was capped, removed from the glove box, sparged 3 times to 500 pounds per square inch gauge (psig) with a 1:1 hydrogen/carbon monoxide gas mixture and heated quickly to 130° C. At maximum temperature the gas pressure was adjusted to 950 psig. After 5 hours of reaction time 40% of the olefin had been converted to $C_{15}$ aldehydes. Comparison with the product obtained in EXAMPLES 2, 3, and 5 shows the swollen catalyst to be much more effective than that of the instant invention.

EXAMPLE 7

The catalyst of Example 6 (1 gram) was swollen in 35 ml of benzene for 2 hours. This suspension was then transferred in an argon-filled glove box to an autoclave and 35 grams (0.208 mole) of 1-dodecene was added to the reactor. The autoclave was capped, removed from the glove box and sparged 3 times to 900 psig with a 1:1 hydrogen/carbon monoxide gas mixture. The reactor was then pressured to 700 psig with the same gas mixture heated quickly to 120° C. and the reactor gas pressure adjusted to 930 psig at maximum temperatures. After 5 hours of reaction time, vapor phase chromatography analysis showed 90% conversion of the olefin to $C_{13}$ aldehydes.

Example 8 shows the synthesis of the catalyst wherein no intermediate alkyl group is present between the 6-member ring and the 5-member ring.

EXAMPLE 8

The polystyrene described above (1% divinylbenzene crosslinked) was brominated according to the procedure taught in the *Journal of American Chemical Society*, volume 96, 6469 (1974), Relles and Schluenz, to a bromine content of 41%. Thereafter in an argon-filled glove box 10 grams (0.051 mole of bromine) of the brominated polystyrene was swollen in 80 mls of anhydrous oxygen-free THF for one hour. The suspension is then cooled to −78° C. and 38 grams of 18% sodium cyclopentadienide is added over the course of 10 minutes with rapid stirring. The stirred mixture is allowed to warm to room temperature and stirring is continued for 168 hours. The resulting polymer was then filtered and washed with 100 mls THF for 1 hour, 150 mls of acetone for 1 hour, 150 mls of CHCl₃ for 1 hour, then refiltered and dried at 70° C. at 1 tor pressure for 12 hours. A modified polymer (9.5 grams was collected which had the structure

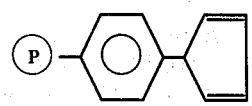

Other methods for preparation of the polymer to this point in the synthesis can be found as previously described. Clearly, a choice of methods can be used to this point in the synthesis.

The recovered polymer was then swollen in THF for 1 hour at which time 150 mls of 1.6 molar and butyl lithium was slowly added over a 10 minute period. The mixture was stirred for 24 hours and is filtered, washed twice with 50 ml portions of dry THF and refiltered yielding a polymer having the structure

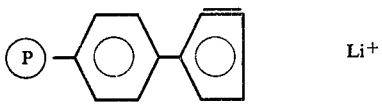

The polymer is then added to 50 mls of dry THF and a weight of [Rh(CO)$_2$X] equal to (0.5) (L) (M) (A) (W) is added to the stirring solution, wherein L equals moles of C$_5$H$_5$ substitution per gram of polymer, M is equal to grams of polymer being converted, A is the percent desired rhodium substitution expressed in decimal, W is the molecular weight of the [RH(CO)$_2$X]$_2$ compound. After addition, stirring is continued for 120 hours. The product is filtered, and the filtered product is extracted with THF or benzene for from 48 to 72 hours and is dried at 25° C. at 0.014 torr for 12 hours, yielding a polymeric catalyst having the structure

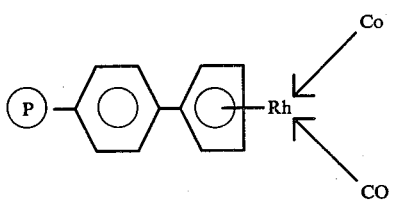

The (pentahaptocyclopentadienyl)biscarbonylrhodium attached to the halo methylated polystyrene has also been found to be an extremely active hydrogenation catalyst at hydrogen pressures of from about 100–3,000 pounds per square inch gauge (psig) and temperatures of from 20° C. to 140° C. for the reduction of various organic functions. This catalyst is thus a dual catalyst, functioning both as a hydroformylation catalyst and a catalyst useful for the reduction of the resulting aldehydes to alcohols. The functions of this catalyst are shown in the examples below. All olefins used were percolated through silica gel before use.

Example 9 shows the reduction of olefins and benzene, example 10 shows the hydrogenation of a second olefin, example 12 shows hydrogenation of an aldehyde, and example 13 shows a continuous one-reactor process of olefin to aldehyde and hydrogenated to alcohol.

EXAMPLE 9

One gram of the catalyst described (containing 4.6% rhodium) was swollen in 35 ml of benzene for 30 minutes. A stainless steel autoclave was then charged with this resulting suspension and 35.2 grams of 1-dodecene (0.207 moles) was added. The autoclave was capped, removed from the inert atmosphere glove box, sparged 3 times to 500 psig with pure hydrogen, and then heated quickly to 110° C. At maximum temperature the hydrogen pressure was adjusted to 600 psig. After 16 minutes of reaction time vapor phase chromatography (vpc) showed total olefin conversion to alkene. Only n-dodecane and benzene were observed to be present. After 30 minutes had passed from the start of the reaction, vpc indicated that 16.1% of the benzene present in the reactor had been fully hydrogenated to cyclohexane.

EXAMPLE 10

The catalyst was recovered from Example 9 and reswollen in 35 ml of benzene of 30 minutes. This reaction was carried out identically to Example 1 except that the reaction temperature was lowered to 100° C. and the pressure reduced to 400 psig hydrogen. Vpc indicated that all of the 1-dodecene had been converted to n-dodecane after 20 minutes of reaction time. After 75 minutes of reaction time 33.7% of the benzene present in the reactor had been hydrogenated to cyclohexane.

EXAMPLE 11

The catalyst was recovered and reswollen in an identical manner to Example 10 and the reactor identically charged with olefin. The reaction was carried out identically to Example 9 except that the reaction temperature was reduced to 80° C. and the reaction pressure reduced to 100 psig hydrogen. After 140 minutes reaction time vpc indicated that 20% of the olefin had been converted to n-dodecane. The reaction pressure was then increased to 620 psig hydrogen and within 14 minutes of the pressure increase, 100% of the olefin had been hydrogenated to n-dodecane and 10.6% of the benzene solvent had been reduced to cyclohexane.

EXAMPLE 12

The catalyst was recovered and reswollen as described in Example 10. The reactor was charged with 23.6 grams of aldehyde made from the hydroformylation of 7-tetradecene by this same catalyst under the hydroformylation conditions specified in Examples 2, 3, and 5. The catalyst suspension was added, the reactor heated to 110° C., and pressured to 1,000 psig hydrogen. After 2½ hours vpc indicated 93.3% of the C$_{14}$-C$_{15}$ aldehydes had been converted to C$_{14}$-C$_{15}$ alcohols.

EXAMPLE 13

In an argon filled water-free glove box 35 grams of 7-tetradecene (0.178 moles) and 1 gram of catalyst were swollen in 35 ml of benzene. The autoclave was then capped and removed from the box. The reactor was purged 3 times to 900 psig with a 1:1 gas mixture of CO/H$_2$ and then quickly heated to 110° C. Upon attaining maximum temperature the reactor gas pressure was adjusted to 900 psig CO/H$_2$ and the reaction allowed to continue for 320 minutes at which time analysis of the reactor contents indicated in 95.2% conversion of C$_{14}$ olefin to C$_{15}$ aldehydes.

The reactor was then disconnected from the H$_2$/CO tank and reconnected to a source of pure hydrogen. The reactor was purged to 900 psig 12 times with hydrogen and reheated to 110° C. When temperature was reached, the pressure of hydrogen was adjusted to 1000 psig. The reaction was allowed to continue for 150 minutes at which time analysis indicated a 94% conversion of C$_{15}$ aldehydes to C$_{15}$ alcohols.

The instant invention thus provides a hydroformylation catalyst containing no toxic Group V ligands, yet capable of efficient conversion of internal and primary olefins to aldehydes.

While certain embodiments and details have been shown for the purpose of illustrating this invention, it will be apparent to those skilled in this art that various changes and modifications may be made herein without departing from the spirit or the scope of the invention.

I claim:

1. A catalyst having a structure selected from the group consisting of

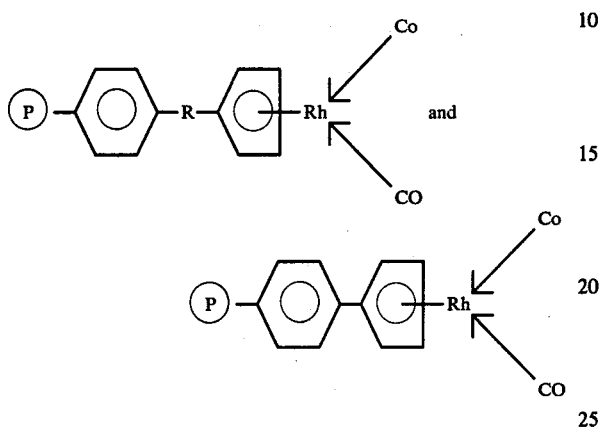

wherein R is an alkyl group containing from 1 to 10 carbon atoms, and (P) represents a polystyrene polymer.

2. A catalyst as described in claim 1 wherein R is an alkyl group containing from 1 to 10 carbon atoms.

3. A catalyst as described in claim 2 wherein R is an alkyl group containing from 1 to 3 carbon atoms.

4. A method of preparing a catalyst of the formula

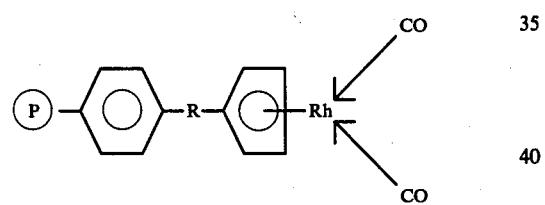

wherein R is an alkyl group containing from 1 to 10 carbon atoms and (P) is a polystyrene polymer backbone, under an inert atmosphere, comprising, (a) dissolving a compound having the structure

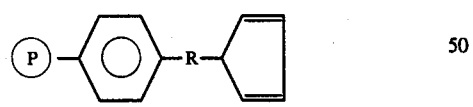

in a suitable solvent, wherein (P) and R have the meaning described above, and reacting with (b) an alkyl or aryl organolithium material containing from 1–10 carbon atoms, continuing agitation for a period of time sufficient to effect reaction;

(c) filtering the polymer from solution, readding to a suitable solvent, and adding [Rh(CO)₂X]₂ wherein X is a halogen; and (d) continuing stirring for a sufficient time to effect reaction, then removing the catalyst from solution extracting with a suitable solvent, and drying prior to use.

5. A method as described in claim 4 wherein the alkyl or aryl organolithium material is selected from the group consisting of n-butyl lithium, methyl lithium, ethyl lithium, propyl lithium, phenyl lithium, s-butyl lithium, or t-butyl lithium.

6. A method as described in claim 5 wherein the solvents suitable for the method are selected from the group consisting of tetrahydrofuran, benzene, xylenes, toluene, acetophenone, and dimethylformamide.

7. A method of preparing a catalyst of the formula

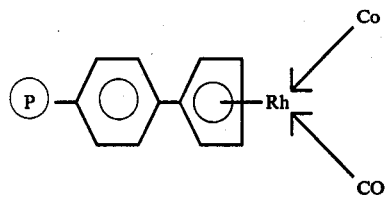

wherein (P) is a polystyrene polymer backbone, comprising, under an inert atmosphere;

(a) dissolving a polymer having the general formula;

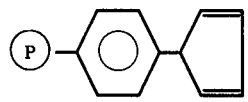

in a suitable solvent and adding an alkyl or aryl organolithium compound, stirring for sufficient time to effect reaction, filtering the polymer from solution and washing with a suitable solvent before refiltering to yield a polymer having the general formula;

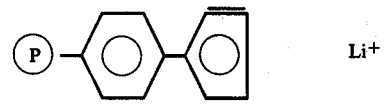

(b) then adding recovered polymer to a suitable solvent and adding sufficient [Rh(CO)₂X]₂, wherein X is a halogen to provide the desired percentage of rhodium and agitating the mixture for sufficient time to effort reaction;

(c) recovering the polymer, washing with a suitable solvent, and drying to yield a polymeric catalyst having the structure;

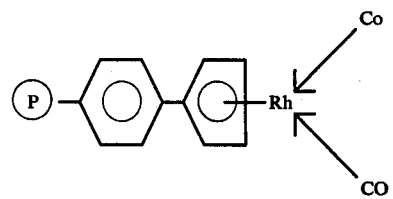

8. A method as described in claim 7 wherein the alkyl or aryl organolithium material is selected from the group consisting of n-butyl lithium, methyl lithium, ethyl lithium, propyl lithium, phenyl lithium, s-butyl lithium, or t-butyl lithium.

9. A method as described in claim 7 wherein the solvents suitable for the method are selected from the group consisting of the tetrahydrofuran, benzene, xylenes, toluene, acetophenone, and dimethylformamide.

* * * * *

Notice of Adverse Decision in Interference

In Interference No. 100,598, involving Patent No. 4,173,575, J. T. Carlock, POLYMER BOUND (PENTAHAPTOCYCLOPENTADIENYL) BIS CARBONYL RHODIUM HYDROFORMYLATION CATALYST, final judgment adverse to the patentee was rendered Aug. 13, 1981, as to claims 1-9.

[*Official Gazette November 3, 1981.*]